United States Patent [19]

Su et al.

[11] Patent Number: 4,910,303

[45] Date of Patent: Mar. 20, 1990

[54] PROCESS FOR PREPARING OXAZINE DERIVATIVES

[75] Inventors: Wei-Yang Su; John F. Knifton, both of Austin, Tex.

[73] Assignee: Texaco Chemical Company, White Plains, N.Y.

[21] Appl. No.: 198,903

[22] Filed: May 26, 1988

[51] Int. Cl.$^4$ ............................................. C07D 265/30
[52] U.S. Cl. ..................................................... 544/98
[58] Field of Search ........................................... 544/98

[56] References Cited

U.S. PATENT DOCUMENTS

| | | | |
|---|---|---|---|
| 3,766,179 | 10/1973 | Snapp et al. | 544/98 |
| 4,068,077 | 1/1978 | Goetz et al. | 544/178 |
| 4,670,557 | 6/1987 | Su | 544/173 |

*Primary Examiner*—Richard L. Raymond
*Attorney, Agent, or Firm*—Jack H. Park; Kenneth R. Priem; Cynthia L. Kendrick

[57] ABSTRACT

This invention relates to the reaction of N-alkyl-bis-(2-hydroxyalkyl)amines to form oxazine derivatives by a process comprising reacting said amines in the presence of a ruthenium-containing compound and hydrogen acceptor.

2 Claims, No Drawings

PROCESS FOR PREPARING OXAZINE DERIVATIVES

FIELD OF THE INVENTION

This invention relates to the preparation of oxazine derivatives by reactin N-alkyl-bis-(2-hydroxyalkyl) amines in the in the presence of a ruthenium-containing compound and a hydrogen acceptor.

More specifically, this invention concerns the reaction of N-alkyl-bis(2-hydroxyalkyl)amines in the presence of a ruthenium-containing compound and a hydrogen acceptor to yield 3,4-dihydro-3,4,6-trialkyl-2H-1,4-oxazines such as 3,4-dihydro-2,4,6-trimethyl-2H-1,4-oxazine and 3,4-dihydro-4-t-butyl-2,6-dimethyl-2H-1,4-oxazine. These oxazine derivatives can be used as urethane catalysts and they are also potentially useful as pharmaceutical intermediates.

BACKGROUND OF THE INVENTION

Catalysts containing ruthenium and phosphorous have been found to promote hydrogen transfer from alcohols, other hydrocarbons, aldehydes, acids, amides and other hydrogen donors.

In an article titled "Dichlorotris(triphenylphosphine)ruthenium-catalyzed Hydrogen Transfer from Alcohols to Saturated and $\alpha,\beta$-Unsaturated Ketones", Sasson, e al. discuss the use of the ruthenium compound as an efficient catalyst for selective transfer hydrogenation of $\alpha,\beta$-unsaturated ketones by primary and secondary carbinols. In this reference kinetic studies were carried out using 1-phenyl-ethanol as a hydrogen donor and benzylideneacetophenone as an acceptor. (See *J. Org. Chem.* (1975), 40. 1887)

Another group has studied regioselective dehydrogenation and reported their findings in *J. Org. Chem.* (1986), 51. 2034. In an article titled "Ruthenium Complex Catalyzed Regioselective Dehydrogenation of Unsymmetrical $\alpha,\omega$-Diols", Ishii, et al. of the University of Tokyo, studied the ruthenium complex catalyzed regioselective dehydration of unsymmetrically substituted 1,4- and 1,5-diols in the presence of a hydrogen acceptor such as an $\alpha,\beta$-unsaturated ketone to give predominantly $\beta$-substituted $\gamma$-lactones and $\gamma$-substituted $\delta$-lactones, respectively. One of the hydrogen acceptors used was 4-phenyl-3-buten-2-one.

In an article in *J. Org. Chem.* (1963), 28, 448, Dillard et al. discuss various methods of preparing substituted N-(2-hydroxyalkyl)propargylamines; and, their cyclization and subsequent hydrogenation to various morpholine derivatives is reported.

These references do not appear to discuss the synthesis of oxazine derivatives from bis-hydroxyalkylamines, nor do they discuss a novel method for using hydrogen acceptors to prevent the oxazine derivatives from being reduced to morpholine.

In related, coassigned U.S. Pat. No. 4,770,557, a method is disclosed for the preparation of hydroxymorpholines from aliphatic epoxides in the presence of a ruthenium-containing compound with a phosphine ligand at a temperature of 150° C. to 190° C. and a pressure of at least one atmosphere.

In a process for producing morpholines it would be an advance in the art to devise a process for alternatively producing oxazine derivatives and preventing reduction to morpholines by use of a hydrogen acceptor, particularly using mild conditions.

In the instant invention similar experimental conditions were used, as in U.S. Pat. No. 4,670,57, except a hydrogen acceptor was employed along with a ruthenium-containing compound and said acceptor functioned to prevent theoxazine derivatives (A In Eq. 1) from being reduced to morpholines.

This can be represented by the following equation:

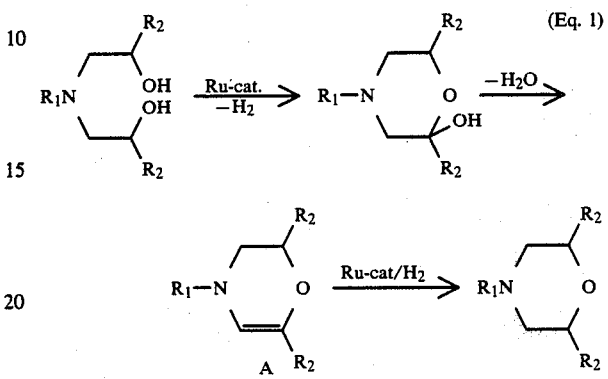

Under similar conditions the N-alkyl-bis-(2-hydroxyalkyl)amines could be converted to corresponding morpholines in the absence of a suitable hydrogen acceptor, however with the hydrogen acceptor the oxazine derivatives can be produced in good yields.

SUMMARY OF THE INVENTION

In accordance with the present invention N-alkyl-bis-(2-hydroxyalkyl)amines are reacted in the presence of a ruthenium-containing compound and a hydrogen acceptor to produce oxazine derivatives at a temperature of 100°–400° C. and a pressure of subatmospheric to 1000 psi. The yield of 3,4-dihydro-trialkyl substituted-2H-1,4-oxazines reaches as high as 65%. (See Example I)

DETAILED DESCRIPTION OF THE INVENTION

In the narrower and more preferred practice of this invention 3,4-dihydro-2,4,6-trialkyl-2H-1,4-oxazines are prepared from N-alkyl-bis-(2-hydroxyalkyl)amines by a process which comprises reacting said amine in the presence of a ruthenium-containing compound with a hydrogen acceptor and a solvent at a pressure of at least subatmospheric and a temperature of at least 50° C. until there is substantial formation of the desired oxazine derivatives.

The general reaction for reacting bis-(2-hydroxyalkyl)amines in the presence of ruthenium catalyst and a hydrogen acceptor under mild conditions can be represented by:

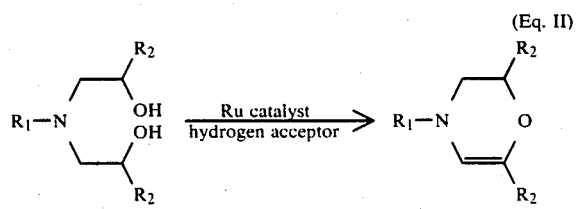

All the oxazine derivatives reported in the invention are new compounds. See, for example, U.S. Pat. No. 4,068,077 (1978).

The oxazine derivative, such as 3,4-dihydro-2,4,6-trimethyl-2H-1,4-oxazine, as evidenced by Example 5, have been demonstrated to be useful as urethane catalysts in standard laboratory tests. In addition, the oxazine derivatives are potentially useful as pharmaceutical intermediates.

Recovery of the oxazine derivatives and by-products from the reaction product can be carried out in any convenient or conventional manner such as by distillation, extraction etc.

In general, the components of the reaction mixture, including the bis-alkanolamine, ruthenium-containing compound, hydrogen acceptor and solvent may be added in any sequence, preferably with good agitation, to provide a good dispersion or a homogeneous reaction mixture. For example, the following represent some variations insofar as the addition of catalyst components, solvent and bis-(2-hydroxyalkyl)amines addition that can be made without departing from the inventive process. These modifications include:

1. The catalyst may be preformed and added to the solvent prior to addition of the N-alkyl-bis-(2-hydroxyalkyl)amines, hydrogen acceptors and other reactants.

2. Preferably, to minimize stability problems with the catalyst, the catalyst is best formed in situ, usually by mixing the solvent and bis-(2-hydroxy)amine followed by the addition of the ruthenium-containing compound and phosphorous-containing compound to form the reaction mixture.

3. After using either variation 1 or 2 the catalyst containing reaction mixture is heated until the product is formed.

The reactant used in the process of this invention comprises an N-methyl bis-(2-hydroxypropyl)amine.

The catalyst system consists of a ruthenium-containing compound in conjunction with a phosphine ligand, a hydrogen acceptor and a solvent.

In the practice of this invention N-alkyl-bis-(2-hydroxyalkyl)amines of the formula:

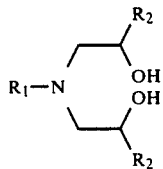

are reacted to give the desired oxazine derivatives. Suitable N-alkyl-bis-(2-hydroxyalkyl)amine reactants are those where $R_1$ and $R_2$ are the same, or different, and represent an alkyl, aryl, or aralkyl, a hydrocarbon radical containing 1 to 12 carbons, and preferably from 1 to 4. Preferred hydrocarbons comprise alkyl groups, including methyl, ethyl, n-propyl, isopropyl, n-butyl and t-butyl.

Examples of N-alkyl-bis-(2-hydroxyalkyl)amines that are suitable reactants in the desired syntheses of oxazine derivatives include N-methyl-bis-(2-hydroxypropyl)amine, N-t-butyl-bis-(2-hydroxypropyl)amine, N-n-butyl-bis-(2-hydroxypropyl)amine and N-isopropyl-bis-(2-hydroxypropyl)amine.

The ruthenium-containing compound to be used in the catalyst in the practice of this invention may be chosen from a wide variety of organic or inorganic compounds, complexes, etc. as will be shown and illustrated below. It is only necessary that the catalyst precursor actually employed contain said ruthenium in any of its ionic states. The actual catalytically active species is then believed to comprise ruthenium in complex combination with one or more phosphine promoters, the hydrogen acceptor and a solvent.

The ruthenium catalyst precursors may take many different forms. For instance, the ruthenium may be added to the reaction mixture in an oxide form, as in the case of, for example, ruthenium(IV) oxide hydrate. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium(III) chloride and ruthenium nitrate, or as the salt of a suitable organic carboxylic acid, such as, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydridocarbonyl derivative. Here, suitable examples include triruthenium dodecacarbonyl and other hydridocarbonyls such as $H_2Ru_4(CO)_{13}$ and $H_4Ru_4(CO)_{12}$, and substituted carbonyl species such as the trccarbonylruthenium(II) chloride dimer, $[Ru(CO)_3C_{12}]_2$.

Preferred ruthenium-containing compounds include ruthenium salts of a mineral acid. Among these, particularly preferred is ruthenium chloride.

In addition to the ruthenium source the preferred catalyst includes a tertiary phosphine such as a trialkyl phosphine or a triarylphosphine such as tripeenylphosphine. A preferred example is ruthenium trichloride in the presence of an excess of trihenylphosphine.

Suitable tertiary phosphine components comprising the preferred catalyst formulations may contain one or more trivalent phosphorus atoms per molecule, bonded to alkyl, aryl, alkaryl and aralkyl radicals, or mixtures thereof. Specific examples of such tertiary phosphines include tri-n-butylphosphine, tri-sec-butylphosphine, trimethylphosphine, triethylphosphine, tri-c-hexylphosphine, triphenylphosphine, tri-p-tolylphosphine, benzyldiphenylphosphine, tri-p-methoxyphenylphophine, as well as 1,2-bis(dibenzylphsphino)ethane
1,2-bis(di-n-butylphosphino)ethane
1,2-bis(dicyclohexylphosphino)ethane
1,-bis(diethylphosphino)ethane
1,2-bis(dimethylphosphino)ethane
1,4-bis(iiphenylphosphino)butane
1,2-bis(dphenylphosphino)ethane
1,6-bis(diphenylphosphino)hexane
1,5-bis(diphenylphosphino)pentane
1,3-bis(diphenylphosphino)propane
1,2-bis(di-n-propylphosphino)ethane
n-butydiphenylphosphine
diehylphenylphosphine
di-n-hexylphenylphosphine
ethyldiphenylphosphine
hexyldiphenlphosphine
tribenzylphosphine, triisobutylphosphine,
tri-n-propylphosphine A hydrogen acceptor is used in conjunction with the ruthenium source and phosphinesource to prevent the oxazine derivatives from being reduced to morpoolines. The hydrogen acceptors should generally be functionality and/or activated aliphatic compounds containing one or more unsaturated carbon-carbon bonds. Suitable hydrogen acceptors include α,β-unsaturated ketones, where said unsaturation is due to one or more olefinic double bonds. Examples include trans-4-phenyl-3-buten-2-one, benzylideneacetophenone, α-methylbenzylideneacetophenone, 4-penten-3-one, 4-methoxybenzylideneacetophenone, 4-chlorobenzylideneacetophenone, 2-cyclohexen-1-one, isomeric dibenzyl-2-cyclohexen-1-ones, benzylidene-4,-methylacetophenone, 4-fluorobenzylideneacetophenone, 3,4-dimethoxybenzylideneacetophenone and related α,β-unsaturated ketones.

The satisfactory performance of trans-4-phenyl-3-buten-2-one,

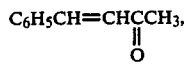

is demonstrated in Examples 1 through 4.

The novel reaction is run most conveniently in the presence of a solvent. The solvent useful in the process of this invention is an oxygenated hydrocarbon, i.e., a compound composed only of carbon, hydrogen and oxygen and one in which the only oxygen atoms present are in ether groups. Generally, the oxygenated hydrocarbon will contain 3 to 14 carbon atoms and preferably a maximum of 7 oxygen atoms. The solvent must be substantially inert under reaction conditions.

Ethers which may be utilized as solvents include cyclic, acyclic and heterocyclic materials. Preferred ethers are the aliphatic ethers such as tetraglyme and triglyme and heterocyclic ethers, as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc. A solvent which functioned well in the reaction was tetraglyme.

In the process of this invention an N-alkyl-bis-(2-hydroxyalkyl)amine is reacted in the presence of the solubilized ruthenium catalyst, a tertiary phosphine, hydrogen acceptor and a solvent to form oxazine derivatives.

Oxazine products that may be synthesized by the process of this invention (Eq. I nd II) include 3,4-dihydro-2,4,6-trisubstituted-2H-1,4-oxazines. Specific examples include: 3,4-dihydro-2,4,6-trimethyl2H-1,4-oxazine; 3,4-dihydro-4-t-butyl-2,6-dimethyl-2H-1,4-oxazine; 3,4-dihydro-4-n-butyl-,6-dimethyl-2H-1,4-oxazine; and 3,4-dihydro-4-isopropyl-2,6-dimethyl-2H-1,4-oxazine.

The reaction, as represented above in Equation II allows up to greater than 99% conversion of N-alkyl-bis-(2-hydroxyalkyl)amine and up to 65% or greater yield of oxazine derivatives.

The temperature range which can be employed for the reaction is a variable which is dependent upon experimental factors including the particular bis-alkylamine compounds employed, the total pressure, the concentrations of reactants and catalyst, and particularly the choice of ruthenium catalyst and solvent, among other things. Using N-methyl-bis-(2-hydroxypropyl)amine as the substrate with $RuCl_3$-$PPh_3$ as a representative catalyst, an operable range is at least 50° C. and preferably from about 100° C. to 400° C. when pressures of subatmospheric or greater are employed. A narrower range of 100° C. to 220° C. represents the most preferred temperature range when the aforementioned bis-alkylamines are reacted.

The pressure range which can be employed for the reaction is a variable which is also dependent on the factors mentioned above. Using $RuCl_3$-triphenylphosphine and tetraglyme as a representative catalyst and solvent, and N-methyl-bis-(2hydroxypropyl)amine as the substrate, an operable pressure range is from subatmospheric to 1000 psig, or more, when a temperature range of from about 100° to 400° C. is employed. A narrower range of from 0 to 350 psig represents the preferred pressure range when the narrower temperature range of 100° C. to 220° C. is employed.

As previously indicated in the discussion of temperatures and pressures required in the reaction, experimental variables are important in arriving at reaction times. Generally, substantial conversions of p to 65% of the amines to oxazine derivatives can almost always be accomplished within 10 hours, with 2 to 6 hours representing the more usual reaction time interval.

In the process of this invention the molar ratio of ruthenium-containing compound to the phosphine ligand is significant. The experimental work performed indicates that an excess of ligand of about at least 3 moles of triarylphosphine for each mole of ruthenium-compound complex is preferred for good selectivity. Generally a ratio of from 1 to 500 moles of tertiary phosphine for each mole of ruthenium-containing compound has been established to yield the product. Preferably a ratio of 3 to 100 moles of tertiary phosphine pr mole of ruthenium compound is employed for good yields of oxazine derivatives. This preferred ratio is based upon the reaction where an N-alkyl-bis-(2-hydroxypropyl)amine is used s the substrate.

Experimental work indicates that an initial molar ratio of 100 moles to 300 moles of N-alkyl bis amine per mole of ruthenium catalyst can be employed in most instances. The minimal ratio would be about 0.001 moles of catalyst per mole of amine.

Products, including 3,4-dihydro-2,4,6-trimethyl-2H-1,4-oxazine and 3,4-dihydro-4-t-butyl-2,6-dimethyl-2H-1,4-oxazine may be isolated by the usual chemical or physical techniques, such as distillation, solvent extraction, chromatography, etc. Identification is by nuclear magnetic resonance and infra-red spectroscopy. Unless otherwise specified all percentages are by weight and all temperatures are in centigrade rather than fahrenheit.

Yield, as defined herein, represents the efficiency in catalyzing the desired reaction relative to other undesired reactions. In this instance synthesis of oxazine derivatives is the desired conversion. Yield is expressed as a molar percentile, and is calculated by determining the molar amount of, for example, 3,4-dihydro-2,4,6-trimethyl-2H-1,4-oxazine product formed, divided by the molar amount of N-alkyl bis amine charged and multiplying the quotient obtained by 100.

Having described the inventive process in general terms, the following examples are submitted to supply specific and illustrative embodiments.

EXAMPLE 1

A mixture of N-methyl-bis-(2-hydroxypropyl)amine (75g, 0.51 mol), trans-4-phenyl-3-buten-2-one (75g, 10.51 mol), ruthenium trichloride hydrate (0.626g 12.3 mmole), triphenylphosphine (2.0g 17.6 mmole), and tetraglyme (30g) was added to a 250-ml 3-neck round bottom flask connected with a fractional distillation set and a thermometer. The reaction was heated to 180° C. under nitrogen and the products were distilled out through the distillation set. The products (organic layer) were then fractionally distilled again to obtain a 65% yield of 3,4-dihydro-2,4,6-trimethyl-2H-1,4-oxazine.

EXAMPLE 2

N-t-butyl-bis-(2-hydroxypropyl)amine (60g, 0.32 mol) and trans-4-phenyl-3-buten-2-one (85g 10.58 mole) were subjected to a reaction as described in Example 1 above, except that the reaction temperature wa 220° C. A 56% yield of 3,4-dihydro-4-t-butyl-2,6-dimethyl-2H-1,4-oxazine was obtained.

EXAMPLE 3

N-n-butyl-bis-(2-hydroxypropyl)amine (60g, 0.32 mol) and trans-4-phenyl-3-buten-2-one (85g 10.58 mole) were subjected to a reaction as described in Example 1 above, except that the products stayed in the reaction flask and the reaction was held at 180° C. for 5 hours. A 51% yield of 3,4-dihydro-4-n-butyl-2,6-dimethyl-2H-1,4-oxazine was obtained.

EXAMPLE 4

N-isopropyl-bis-(2-hydroxypropyl)amine (50g, 0.29 mol) and trans-4-phenyl-3-buten-2-one (90g 1060 mole) were subjected to a reaction as described in Example 1 above, except that the reaction temperature was 220° C. A 57% yield of 3,4-dihyrdro-4-isopropyl-2,6-dimethyl-2H-1,4-oxazine was obtained.

EXAMPLE 5

This example illustrates the use of 3,4-dihydro-2,4,6-trimethyl-2H-1,4-oxazine as urethane catalyst.

A sample of polyester foam was prepared by initially mixing the oxazine (Sample 6218-02 DF-6ª, from Example 1), polyol (FOAMREZ® 53 FROM WITCO Chemical), water, surfactant (L-536) and cocatalyst (ARMEEN® DM16D) into a B-component in the proportions listed below.

Toluene diisocyanate (TDI, A-component) was then added with mixing and the reactants allowed to stand.

| | |
|---|---|
| FOAMREZ® 53 | 100 |
| Water | 3.8 |
| L-536 | 1.0 |
| ARMEEN® DM16D | 0.4 |
| 6218-020F-6 | 1.98 |
| TDI | 44.96 |

| | |
|---|---|
| index | 1.00 |
| ªStructure: | 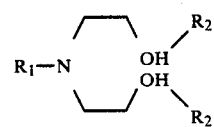 |

What is claimed is:

1. A process for the preparation of an oxazine derivative from the group consisting of 3,4-dihydro-2,4,6-trimethyl-2H-1,4-oxazine, 3,4-dihydro-4-t-buty-2,6-dimethyl-2H-1,4-oxazine, 3,4-dihydro-4-n-butyl-2,6-dimethyl-2H-1,4-oxazine and 3,4-dihydro-4-isopropyl-2,6-dimethyl-2H-1,4-oxazine by the reaction of an N-alkyl-bis-(2-hydroxyalkyl)amine of the formula:

$$R_1-N\begin{pmatrix} \\ \\ \end{pmatrix}\begin{matrix} OH \diagdown R_2 \\ OH \diagdown R_2 \end{matrix}$$

wherein $R_1$ and $R_2$ are the same or different and are methyl, isopropyl, n-butyl or t-butyl in the presence of a catalyst comprising ruthenium halide, a tertiary phosphine and a hydrogen acceptor consisting of an $\alpha,\beta$-unsaturated ketone and a solvent selected from the group consisting of aliphatic ethers and heterocyclic ethers at a temperature from about 100° C. to 220° C. and a pressure of about subatmospheric to 1000 psig.

2. A process for the preparation of an oxazine derivative from the group consisting of 3,4-dihydro-2,4,6-trimethyl-2H-1,4-oxazine, 3,4-dihydro-4-t-butyl-2,6-dimethyl-2-H-1,4-oxazine, 3,4-dihydro-4-n-butyl-2,6-dimethyl-2H-1,4-oxazine and 3,4-dihydrò-4-isopropyl-2,6-dimethyl-2H-1,4-oxazine by the reaction of an N-alkyl-bis-(2-hydroxyalkyl) amine from the group consisting of N-methyl-bis-(2-hydroxypropyl) amine, N-t-butyl-bis(2-hydroxypropyl) amine, N-n-butyl-bis(2-hydroxypropyl) amine and N-isopropyl-bis-(2-hydroxypropyl) amine in the presence of a catalyst consisting of ruthenium trichloride hydrate, triphenylphosphine and a hydrogen acceptor comprising trans-4-phenyl-3-buten-2-one and further in the presence of a solvent from the group consisting of 1,4-dioxane and tetraglyme at a temperature off from 100° C. to 220° C. and a pressure of subatmospheric to 100 psig.

* * * * *

UNITED STATES PATENT AND TRADEMARK OFFICE
CERTIFICATE OF CORRECTION

PATENT NO. : 4,910,303

DATED : March 20, 1990

INVENTOR(S) : Wei-Yang Su et al

It is certified that error appears in the above-identified patent and that said Letters Patent is hereby corrected as shown below:

Claim 1, Col. 8, line 14, "3,4-dihydro-4-t-buty" should read

--3,4-dihydro-4-t-butyl--.

Claim 2, Col. 8, line 50, "off" should read --of--.

Signed and Sealed this

Fifth Day of June, 1990

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,910,303

DATED : March 20, 1990

INVENTOR(S) : Wei-Yang Su and John Frederick Knifton

It is certified that error appears in the above-identified patent and that said Letters Patent is hereby corrected as shown below:

At Col. 8, lines 20-25 delete

"                "

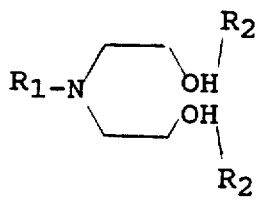

and insert therefor

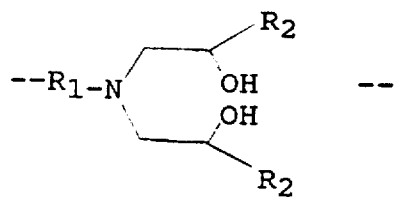

Signed and Sealed this

Nineteenth Day of March, 1991

*Attest:*

HARRY F. MANBECK, JR.

*Attesting Officer*   *Commissioner of Patents and Trademarks*